United States Patent [19]

Cuthbert

[11] Patent Number: 5,352,694
[45] Date of Patent: Oct. 4, 1994

[54] PHARMACEUTICAL AGENTS

[75] Inventor: Murray W. Cuthbert, Macclesfield, England

[73] Assignee: Imperial Chemical Industries PLC, London, England

[21] Appl. No.: 940,138

[22] Filed: Sep. 3, 1992

[30] Foreign Application Priority Data

Sep. 5, 1991 [GB] United Kingdom ............ 91109001.7

[51] Int. Cl.$^5$ ................. C07D 209/08; A61K 31/405
[52] U.S. Cl. .................................... 514/415; 548/469
[58] Field of Search .......................... 514/415; 548/469

[56] References Cited

U.S. PATENT DOCUMENTS 4,918,094  4/1990  Bernstein et al. ................... 514/419

FOREIGN PATENT DOCUMENTS

| 0114950 | 8/1984 | European Pat. Off. . |
| 0290145 | 9/1988 | European Pat. Off. . |
| 0432984 | 6/1991 | European Pat. Off. . |
| 0489547 | 6/1992 | European Pat. Off. . |
| 0489548 | 6/1992 | European Pat. Off. . |
| 0490648 | 6/1992 | European Pat. Off. . |
| 0490649 | 6/1992 | European Pat. Off. . |

OTHER PUBLICATIONS

Gassen, K.; Kirmse, W., "Zun Einfluss von Trifluormethylgruppen auf die Reaktionen aliphatischer Diazonium-Ionen and Carbokationen", *Chem. Ber.*, (1986), 119, 2233–2248.

*Primary Examiner*—Patricia L. Morris
*Assistant Examiner*—Jacqueline Haley
*Attorney, Agent, or Firm*—Thomas E. Jackson

[57] ABSTRACT

A physical form of (R)-3-methoxy-4-[1-methyl-5-(2-methyl-4,4,4-trifluorobutylcarbamoyl)indol -3-ylmethyl]-N-(2-methylphenylsulphonyl) benzamide substantially free of other physical forms, which form is crystalline and has an X-ray powder diffraction pattern with specific peaks at $2\theta = 14.0$, 19.4, 22.0, 22.4 and 24.7°, processes for preparing the form and pharmaceutical compositions containing it. The compound is a leukotriene antagonist useful in the treatment of diseases such as asthma.

6 Claims, 2 Drawing Sheets

PHARMACEUTICAL AGENTS

PHARMACEUTICAL AGENTS

The present invention relates to novel pharmaceutical agents. More particularly it relates to a new physical form of a bamoyl derivative, to a process for its preparation and to pharmaceutical compositions containing it.

European Patent Application publication number 432984 A2 discloses the compound (R)-3-methoxy-4-[1-methyl-5-(2-methyl-4,4,4-trifluorobutylcarbamoyl)indol -3-ylmethyl]-N-(2-methylphenylsulphonyl)benzamide (hereinafter referred to as The Compound), processes for preparing it, and pharmaceutical compositions comprising it. The Compound is reported to be an antagonist of the pharmacological actions of one or more of the arachidonic acid metabolites known as leukotrienes, and may therefore be useful in the treatment of diseases in which leukotrienes are implicated, for example in the treatment of allergic or inflammatory diseases, or of endotoxic or traumatic shock conditions.

Examples 2 and 3 of EP 432984 describe processes for preparing The Compound. In Example 2, The Compound was obtained in the form of a white solid by precipitation from an aqueous solution of hydrochloric acid. In Example 3, it was prepared in the form of a white crystalline solid by crystallisation from a mixture of ethanol and acetone.

The products of the two Examples have been subjected to an X-ray analysis. This analysis has shown that the two products are different physical forms of The Compound. In particular, the product of Example 2 (hereinafter referred to as form A) is amorphous. Its X-ray spectrum has no discernible peaks. However, the product of Example 3 (hereinafter referred to as form B) is crystalline. Its X-ray spectrum has distinctive peaks at $2\theta = 13.4$ and $17.6°$.

The two forms have been studied with a view to their ease of manufacture and suitability for formulation as pharmaceutical agents. Form A has been found to be difficult to manufacture substantially free of other physical forms, and can be morphologically unstable. Furthermore, because it is prepared by precipitation, it needs to be prepared from a chemically pure source of The Compound. Form B has been found to be easier to manufacture substantially free of other physical forms than form A. However, it has been found to be morphologically unstable when subjected to shear forces, for example when it is ground or ball milled. Furthermore, form B has been found to convert at about 110° C. into another crystalline form of The Compound (referred to hereinafter as form C). This form has a melting point of about 142° C., and is believed to have been the physical form to which The Compound converted when the melting point of the product of Example 3 was determined. The ready interconversion of forms B and C makes analysis for their morphological purity difficult, an important procedure in quality assurance checks during the manufacture of a pharmaceutical product.

It has now been found that The Compound may exist in yet another physical form.

Accordingly the invention provides a new physical form of (R)-3-methoxy-4-[1-methyl-5-(2-methyl-4,4,4-trifluorobutylcarbamoyl)-indol-3-ylmethyl]-N-(2-methylphenylsulphonyl)benzamide substantially free of other physical forms, which form is crystalline and has an X-ray powder diffraction pattern with specific peaks at $2\theta = 14.0$, 19.4, 22.0, 22.4 and 24.7°. The form also has an infra-red spectrum (0.5% in KBr) having sharp peaks at 3390, 1620, 1250 and 885 cm.

The new physical form (hereinafter referred to as form D) can readily be manufactured substantially free of other physical forms, and has substantially better morphological stability than either form A or form B.

Where reference is made in this specification to form D substantially free of other physical forms, it preferably means that at least 90% by weight of The Compound present is in that physical form, more preferably at least 95%, for example at least 96, 97 or 98%.

BRIEF DESCRIPTION OF THE DRAWINGS

In this specification, X-ray powder diffraction spectra were determined using 2g of sample material mounted in a Philips standard deep pack holder over the scanning range of $4°$–$40°$ $2\theta$ counting for 4 seconds per point at $0.02°$ intervals to produce a trace of spacings against intensity for this range. An example of an X-ray powder diffraction spectrum for form D is given in FIG. 1.

Infra-red spectra were determined using a 0.5% dispersion of sample material in a potassium bromide disc over the wave number range 4000 to 400cm$^{-1}$. An example of an infra-red spectrum for form D is given in FIG. 2 hereinafter.

Figure 1:
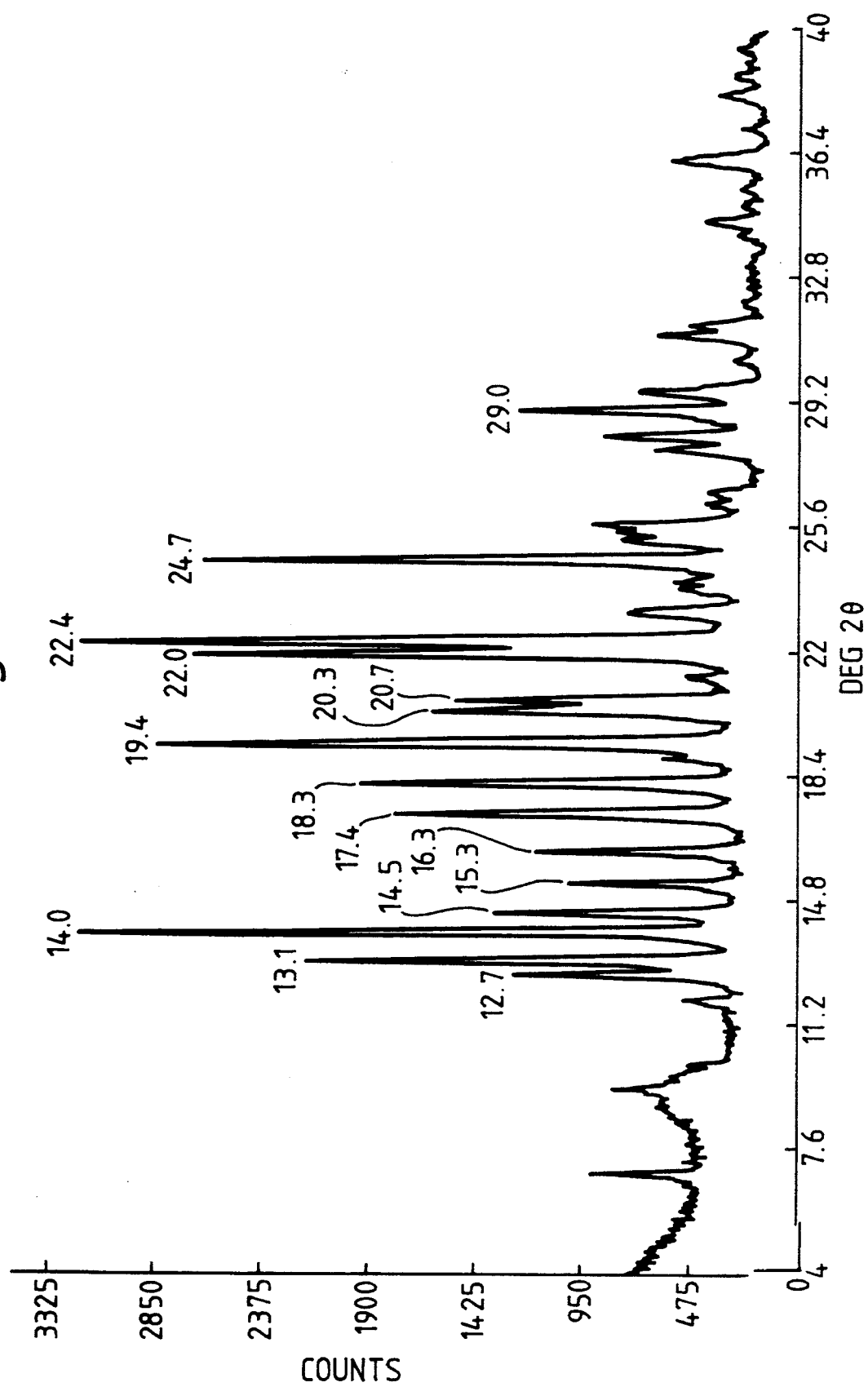
Figure 2:
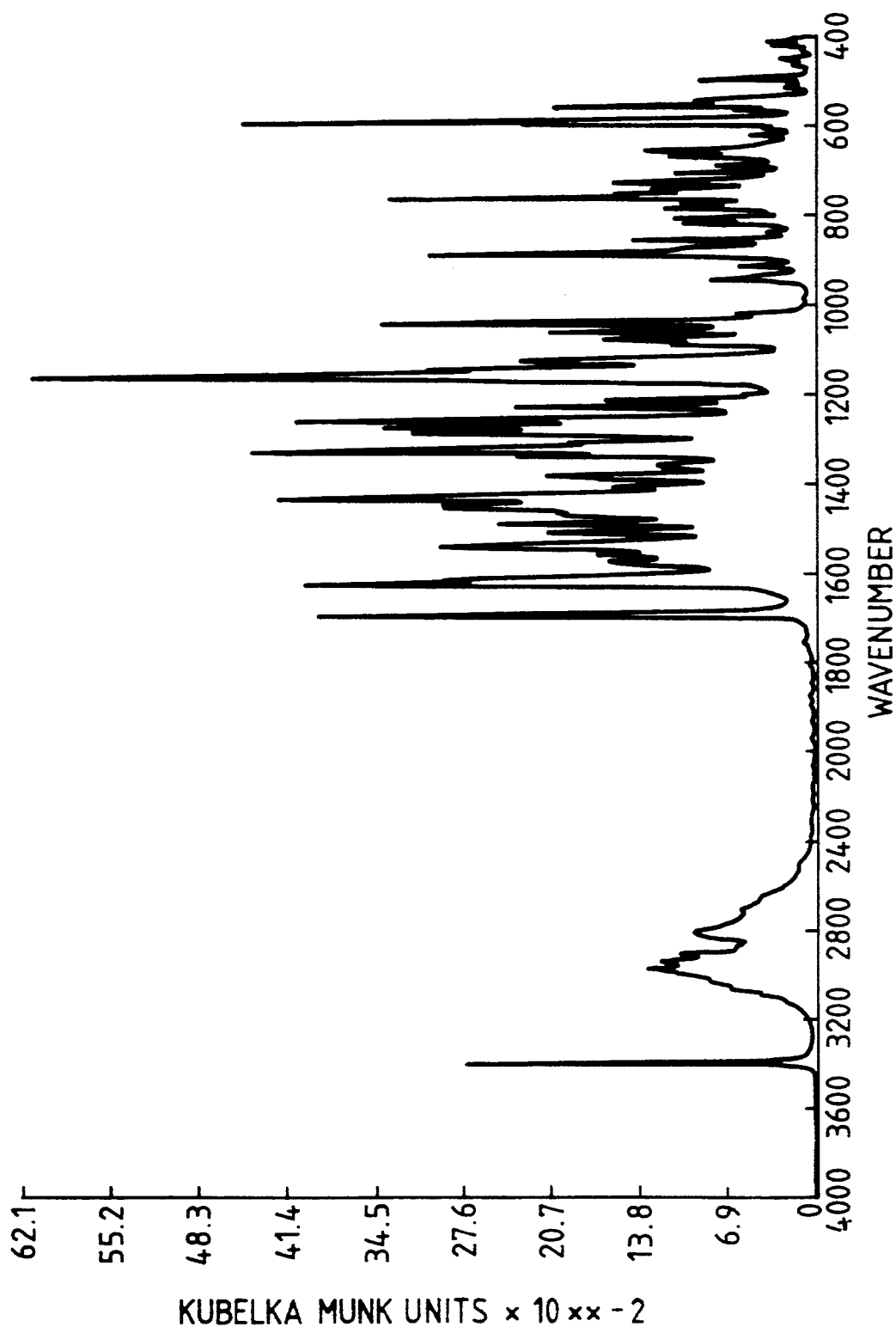

The melting point of form D generally depends upon its level of purity. Typically, form D has been found to have an endotherm maximum determined by differential scanning calorimetry (heating rate 10 ° C./minute) of above 180 ° C., for example 189 ° C.

According to another aspect, the invention provides a process for the preparation of form D substantially free of other physical forms, which comprises forming crystals from a solution of The Compound in a solvent selected from methanol, propanol, isopropanol, ethyl acetate, acetonitrile and dimethoxyethane.

Methanol has been found to give a particularly good yield of crystals in a high state of purity, and is therefore preferred.

The solution is conveniently prepared by dissolving a source of The Compound in the solvent by heating under reflux, reducing the volume of the solvent by evaporation, and then allowing the resultant mixture to cool. For example, when the solvent is methanol, it has been found convenient to dissolve the compound at a concentration of 1 kg/ 15–25 L solvent, then reduce the volume of the solvent to obtain a concentration of 1 kg/8–12 L solvent, and allow the resultant mixture to cool to room temperature.

As stated previously, The Compound possesses leukotriene antagonist properties. Thus, it antagonises the actions of one or more of the arachidonic acid metabolites known as leukotrienes, for example, C$_4$, D$_4$ and/or E$_4$, which are known to be powerful spasmogens (particularly in the lung), to increase vascular permeability and have been implicated in the pathogenesis of asthma and inflammation (see J. L. Marx, Science, 1982, 215, 1380–1383) as well as of endotoxic shock (see J. A- Cook, et al., J. Pharmacol. Exp. Ther., 1985, 235, 470) and traumatic shock (see C. Denzlinger, et al., Science, 1985, 230, 330). The Compound is thus useful in the treatment of diseases in which leukotrienes are implicated and in which antagonism of their action is desired. Such diseases include, for example, allergic pulmonary disorders such as asthma, hay fever and allergic rhinitis and certain inflammatory diseases such as bronchitis, ectopic and atopic eczema, psoriasis, as well as vasospastic cardiovascular disease, and endotoxic and traumatic shock conditions.

Form D may be administered by itself, for example by inhalation in the form of a micronised powder, or in a pharmaceutical composition.

According to another aspect, the invention provides a pharmaceutical composition, which comprises form D substantially free of other physical forms, and a pharmaceutically acceptable carrier.

The pharmaceutical composition may be formulated in a conventional manner, and may typically be in the form of tablets, capsules or suspensions for oral administration; in the form of suppositories for rectal administration; in the form of suspensions for inhalation administration by metered dose inhaler or nebuliser; and in the form of powders together with pharmaceutically acceptable inert solid diluents such as lactose for administration by inhalation.

Form D is also useful as an intermediate for the preparation of a pharmaceutically acceptable solution of The Compound, should a solution formulation be desired.

The amount of form D administered to a patient will depend upon the weight of the patient and the severity of the disorder being treated, and the route of administration. For administration by inhalation, a unit aerosol dose will conveniently comprise from 0.01 to 2.0 mg of form D, preferably from 0.02 to 1.0 mg, more preferably from 0.05 to 0.6 mg. Administration may take place from 1 to 8 times per day, preferably from 1 to 4 times per day. A typical daily dose for a 70 kg patient will be from 0.01 to 16 mg, preferably from 0.02 to 4 mg. For oral administration a tablet or capsule containing up to 250 mg (for example 5 to 100 mg) of form D may be used. A typical daily dose administered orally will be from 0.01 to 25 mg/kg (for example 0.1 to 5 mg/kg).

The following Examples illustrate the invention.

EXAMPLE 1

A solution of The Compound was prepared by dissolving form B (2.02 kg) in methanol (40 L) at 60 ° C. The solution was then cooled to 50 ° C., filtered, and then heated again to remove 20 L of methanol by distillation. The resultant solution was then cooled to 55 ° C., and held at that temperature for 1 hour, cooled to 20 ° C., and then held at that temperature for a further hour. The resultant mixture was then filtered, and the crystalline solid on the filter washed twice with methanol (1×1.5 L, 1×1.0 L). The product was then vacuum dried on the filter, and then vacuum dried in an oven at 50 ° C. to afford 1,555 kg of form D.

As stated hereinbefore, form B may be prepared by the method described in Example 3 of EP 432984. The description of the final stage of this method is reproduced below.

To a mixture of 4-(5-carboxy-l-methylindol-3-ylmethyl) -3-methoxy-N-(2-methylphenylsulfonyl)benzamide (103.5 g), 4-dimethylaminopyridine (112.4 g), and 1-(3-dimethylaminopropyl)-3-ethylcarbodiimide hydrochloride (51.8 g) in tetrahydrofuran (distilled from sodium benzophenone ketyl) (2.0 L), which had been stirred for 2 hours, was added (R)-2-methyl-4,4,4-trifluorobutylamine hydrochloride (42.6 g); and the reaction mixture was stirred overnight (about 18 hours, incomplete reaction) then heated to reflux for two hours (complete reaction). The cooled reaction mixture was diluted with ethyl acetate (2 L) washed with 1N hydrochloric acid (twice) and brine, dried (MgS04) and evaporated. The residue (138.6 g) was combined with impure product from similar procedures (28.0 g) and purified by flash chromatography, eluting with methylene chloride:ethyl acetate (sequentially, 1:0, 9:1 and 3:1) to afford a solid which was triturated twice with ether to give crude (R)-3-methoxy-4-[1-methyl-5-(2-methyl-4,4,4-trifluorobutylcarbamoyl)-indol -3-ylmethyl]-N-(2-methylphenylsulphonyl)benzamide (135.2 g) which was recrystallized from ethanol (1.2 L) and acetone (0.3 L) (concentrated by boiling to about 0.9 L and refrigerated) and dried under vacuum to provide form B (117.1 g, 65% recovery) as a white crystalline solid; mp 141.5°–143.5 ° C.; NHR (300 MHz, DMSO-d$_6$): 1.01 (d, 3H, CH$_3$), 2.0–2.2 (m, 2H, CF$_3$C$_2$), 2.3–2.5 (m, 1H, CHCH$_3$), 2.61 3H, ArCH$_3$), 3.23 (br t, 2H, CH$_2$N), 3.76 (s, 3H, NCH$_3$), 3.92 (s, 3H, OCH$_3$), 4.07 (s, ArCH$_2$Ar'), 7.13 (s, 1H), 7.17 (d, 2H), 7.38–7.69 (m, 6H), 7.72 (d, 1H), 8.05 (d, 1H), 8.11 (s, 1H), 8.46 (br t, 1H, NHCO). Analysis for C$_{31}$H$_{32}$F$_3$N$_3$O$_5$S: Calculated: C, 60.48; H, 5.24; N, 6.83 Found: C, 60.47; H, 5.27; N, 6.67.

The method used to prepare the starting materials used in the method of Example 3 of EP 432984 is summarized in Scheme 1 hereinafter.

EXAMPLE 2

The Compound (100.0g) and methanol (2000ml) are charged to a flask, and a nitrogen purge is started. The mixture is then heated to reflux and held for 30 minutes or until a clear solution is obtained. The solution is then cooled to a temperature in the range 50° to 55° C., and the nitrogen purge is stopped. The solution is then filtered into another flask, and then a nitrogen purge is started. The filtered solution is then heated to reflux, and held under reflux for 10 minutes to ensure complete solution. 1000ml of methanol are then distilled off. The remaining solution is then allowed to cool to ambient temperature, and is then held for one hour at 15° to 20° C. A crystalline product consisting of form D is then filtered off, washed with methanol (100ml) and oven dried at 55° C. under a vacuum. This procedure has been found to afford form D in approximately 90% yield.

COMPARATIVE EXAMPLE 1

0.5 g of form B was ground for 5 minutes using a mortar and pestle. The melting point of the resulting solid was 119°–129° C., characteristic of form A. Differential scanning calorimetry indicated substantial conversion to form A, although some form B was still present.

0.59 of form D was ground for 5 minutes in a mortar and pestle. The melting point of the resulting solid was 180°–183° C. indicating that no morphological change had occurred.

EXAMPLE 3

Form D may be formulated, for example, as follows:(i)

| (i) Tablet 1 | mg/tablet |
|---|---|
| Form D | 100.0 |
| Lactose | 77.5 |
| Polyvinylpyrrolidone | 15.0 |
| Croscarmellose sodium | 12.0 |
| Microcrystalline cellulose | 92.5 |
| Magnesium stearate | 3.0 |

| (i) Tablet 1 | mg/tablet |
|---|---|
| | 300.0 |

| (ii) Tablet 2 | mg/tablet |
|---|---|
| Form D | 20.0 |
| Microcrystalline cellulose | 410.0 |
| Starch | 50.0 |
| Sodium starch glycolate | 15.0 |
| Magnesium stearate | 5.0 |
| | 500.0 |

TABLE 3

| | mg/tablet |
|---|---|
| Form D | 20.0 |
| Microcrystalline cellulose | 100.0 |
| Lactose | 360.0 |
| Sodium starch glycolate | 15.0 |
| Magnesium stearate | 5.0 |

TABLE 3-continued

| | mg/tablet |
|---|---|
| | 500.0 |

| (iii) Capsules 1 and 2 | mg/capsule 1 | mg/capsule 2 |
|---|---|---|
| Form D | 10.0 | 10.0 |
| Colloidal silicon dioxide | 1.5 | 1.5 |
| Lactose | 465.5 | 227.0 |
| Pregelatinised starch | 120.0 | 60.0 |
| Magnesium stearate | 3.0 | 1.5 |
| | 600.0 | 300.0 |

| (iv) Aerosol | mg/can |
|---|---|
| Form D | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

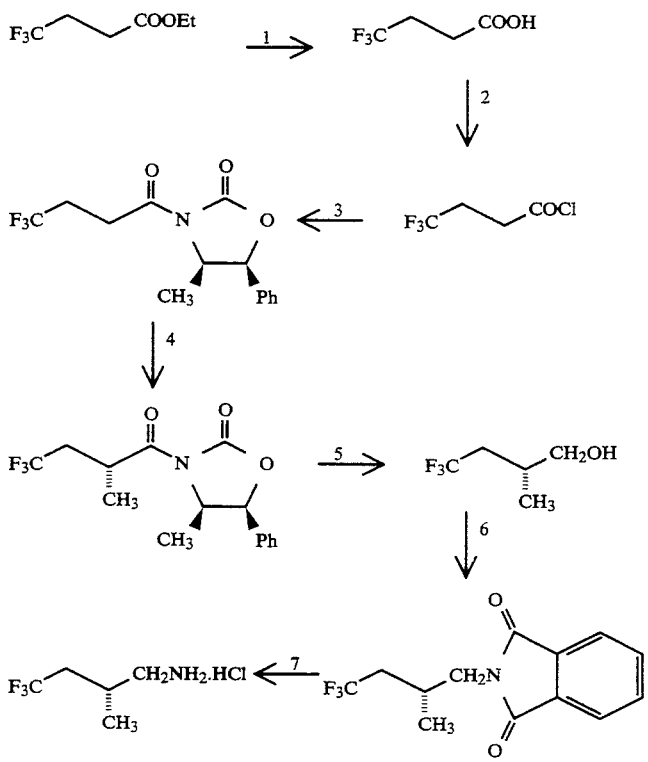

Scheme 1

1. LiOH/H$_2$O
2. (COCl)$_2$
3. (4R, 5S)—(+)-4-methyl-phenyl-2-oxazolidinone
4. Sodium bis(trimethylsilyl)amide, MeI
5. LiAlH$_4$
6. Diethylazodicarboxylate, phthalimide, triphenylphosphine
7. Hydrazine monohydrate, conc. HCl

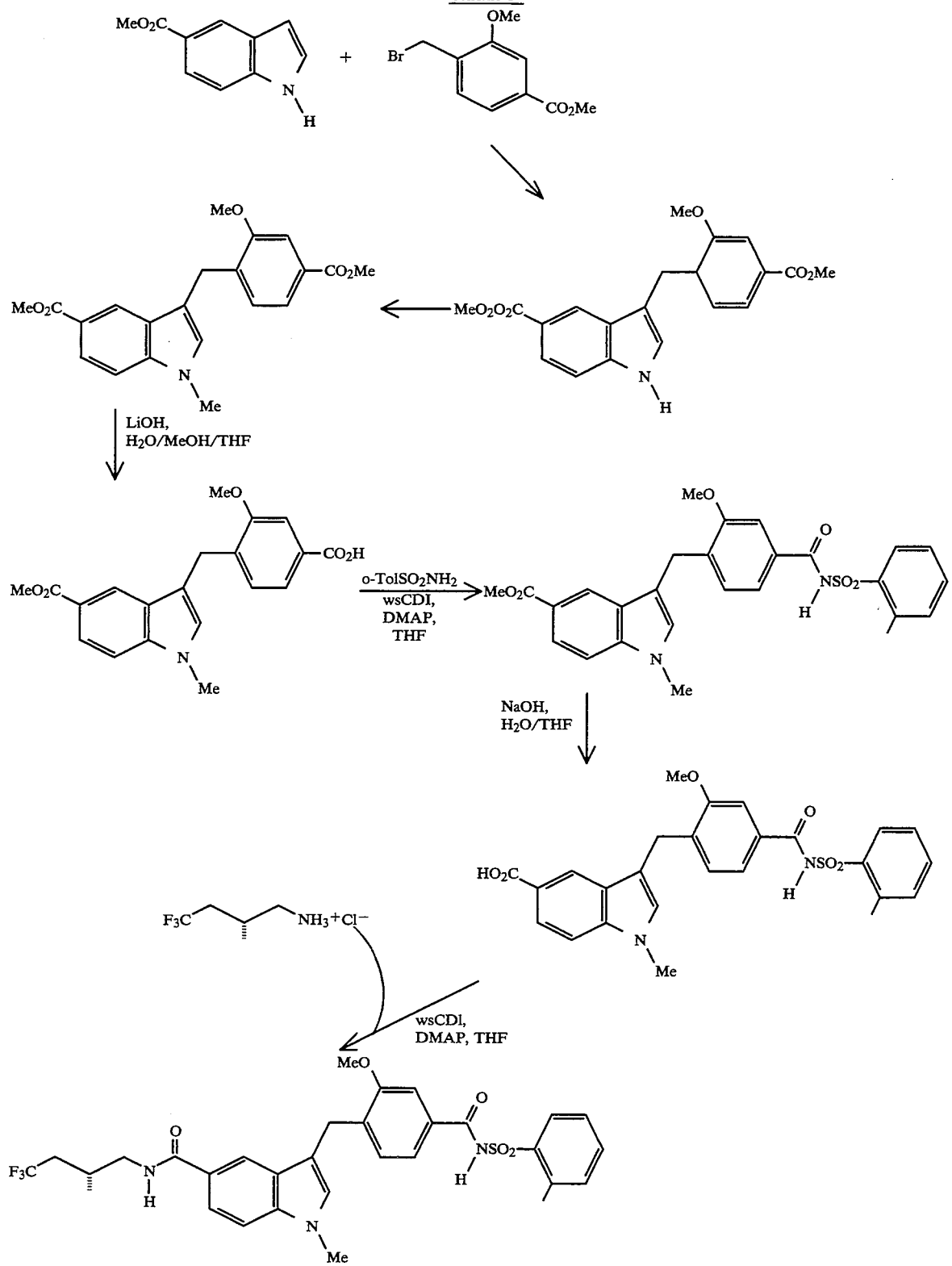

Key
wsDCI 1-(3-dimethylaminopropyl)-3-ethylcarbodiimide hydrochloride
DMAP dimethylaminopyridine
THF tetrahydrofuran

I claim:

1. A physical form of (R)-3-methoxy-4-[1-methyl-5-(2-methyl-4,4,4-trifluorobutylcarbamoyl)indol-3-yl-methyl] - N - (2 - methylphenylsulphonyl)benzamide, which form is crystalline, has an X-ray powder diffraction pattern with specific peaks at $2\theta = 14.0$, 19.4, 22.0, 22.4 and 24.7°, has an infra-red spectrum (0.5% in KBr)

having sharp peaks at 3390, 1620, 1250 and 885 cm$^{-1}$, and has a melting point of 180°–183° C.

2. A physical form of (R)-3-methoxy-4-[1-methyl-5-(2-methyl-4,4,4-trifluorobutylcarbamoyl)indol-3-yl-methyl]-N-(2-methylphenylsulphonyl)benzamide, which form is crystalline, has an X-ray powder diffraction pattern with specific peaks at $2\theta = 14.0, 19.4, 22.0, 22.4$ and 24.7°, has an infra-red spectrum (0.5% in KBr) having sharp peaks at 3390, 1620, 1250 and 885 cm$^{-1}$, and has an endotherm maximum determined by differential scanning calorimetry (heating rate 10° C/minute) of above 180° C.

3. A physical form of (R)-3-methoxy-4-[1-methyl-5-(2-methyl-4,4,4-trifluorobutylcarbamoyl)indol-3-yl-methyl]-N-(2-methylphenylsulphonyl)benzamide as claimed in claim 2, which form has an endotherm maximum determined by differential scanning calorimetry (heating rate 10° C/minute) of above 189° C.

4. A pharmaceutical composition, which comprises a pharmaceutically acceptable carrier and a physical form of (R)-3-methoxy-4-[1-methyl-5-(2-methyl-4,4,4-trifluorobutylcarbamoyl)indol-3-ylmethyl]-N-(2-methylphenylsulphonyl)benzamide, which form is crystalline, has an X-ray powder diffraction pattern with specific peaks at $2\theta = 14.0, 19.4, 22.0, 22.4$ and 24.7°, has an infra-red spectrum (0.5% in KBr) having sharp peaks at 3390, 1620, 1250 and 885 cm$^{-1}$, and has a melting point of 180–183° C.

5. A pharmaceutical composition, which comprises a pharmaceutically acceptable carrier and a physical form of (R)-3-methoxy-4-[1-methyl-5-(2-methyl-4,4,4-trifluorobutylcarbamoyl)indol-3-ylmethyl]-N-(2-methylphenylsulphonyl)benzamide, which form is crystalline, has an X-ray powder diffraction pattern with specific peaks at $2\theta = 14.0, 19.4, 22.0, 22.4$ and 24.7°, has an infra-red spectrum (0.5% in KBr) having sharp peaks at 3390, 1620, 1250 and 885 cm$^{-1}$, and has an endotherm maximum determined by differential scanning calorimetry (heating rate 10° C/minute) of above 180° C.

6. A pharmaceutical composition, as claimed in claim 5, in which the physical form of (R)-3-methoxy-4-[1-methyl-5-(2-methyl-4,4,4-trifluorobutylcarbamoyl)indol-3-ylmethyl]-N-(2-methylphenylsulphonyl)benzamide has an endotherm maximum determined by differential scanning calorimetry (heating rate 10° C/minute) of 189° C.

* * * * *

UNITED STATES PATENT AND TRADEMARK OFFICE
CERTIFICATE OF CORRECTION

PATENT NO. : 5,352,694
DATED : October 4, 1994
INVENTOR(S) : Murray W. Cuthbert

It is certified that error appears in the above-identified patent and that said Letters Patent is hereby corrected as shown below:

Cover Page [30], "United Kingdom..........91109001.7" should read --United Kingdom..........9119001.7--.

Column 7, Claim 1, line 2, "-3-yl-meth-" should read ---3-ylmeth---.

Column 9, Claim 2, line 4, "-3-yl-meth-" should read ---3-ylmeth---.

Column 9, Claim 3, line 14, "-3-yl-meth-" should read ---3-ylmeth---.

Column 10, Claim 5, line 8, "(2-meth-yl-" should read --(2-methyl---.

Signed and Sealed this

Thirtieth Day of May, 1995

Attest:

BRUCE LEHMAN

*Attesting Officer*     *Commissioner of Patents and Trademarks*